(12) United States Patent  
Landesberg

(10) Patent No.: US 6,406,422 B1
(45) Date of Patent: Jun. 18, 2002

(54) VENTRICULAR-ASSIST METHOD AND APPARATUS

(75) Inventor: Amir Landesberg, Haifa (IL)

(73) Assignee: Levram Medical Devices, Ltd., Nesher (IL)

( * ) Notice: Subject to any disclaimer, the term of this patent is extended or adjusted under 35 U.S.C. 154(b) by 0 days.

(21) Appl. No.: 09/517,834

(22) Filed: Mar. 2, 2000

(51) Int. Cl.$^7$ .............................................. A61M 1/12
(52) U.S. Cl. ...................................................... 600/17
(58) Field of Search ...................... 600/16–18; 623/2.1, 623/3.16–3.23, 3.28

(56) References Cited

U.S. PATENT DOCUMENTS

| | | |
|---|---|---|
| 2,982,511 A | 5/1961 | Connor |
| 3,279,464 A | 10/1966 | Kline |
| 3,409,913 A | 11/1968 | Kantrowitz |
| 3,553,736 A | 1/1971 | Kantrowitz |
| 3,568,214 A | 3/1971 | Goldschmied |
| 3,604,016 A | 9/1971 | Robinson |
| 3,668,708 A | 6/1972 | Tindal |
| 3,827,426 A | 8/1974 | Page |
| 3,885,251 A | 5/1975 | Pedroso |
| 4,058,855 A | 11/1977 | Runge |
| 4,144,595 A | 3/1979 | Unger |
| 4,195,623 A | 4/1980 | Zeff |
| 4,230,096 A | 10/1980 | Zeff |
| 4,245,622 A | 1/1981 | Hutchins, IV |
| 4,254,622 A | 3/1981 | Denson, Sr. |
| 4,314,550 A | 2/1982 | Apstein |
| 4,453,537 A | 6/1984 | Spitzer |
| 4,536,893 A | 8/1985 | Parravicini |
| 4,573,997 A | 3/1986 | Wisman et al. |
| 4,583,523 A | 4/1986 | Kleinke et al. |
| 4,621,617 A | 11/1986 | Sharma |
| 4,630,597 A | 12/1986 | Kantrowitz |
| 4,643,733 A | 2/1987 | Becker |

(List continued on next page.)

FOREIGN PATENT DOCUMENTS

| | | |
|---|---|---|
| WO | WO95/28974 | 2/1995 |
| WO | WO 95/28974 | 11/1995 |
| WO | WO98/06454 | 2/1998 |

*Primary Examiner*—George R. Evanisko
(74) *Attorney, Agent, or Firm*—Herbert Dubno

(57) ABSTRACT

A system for ventricular-assist of the normal heart action utilizes an intraventricular device with a limited volume which is expanded at a critical time, for a critical duration and with a volume change course such that it assists the pumping action of the heart without inducing stretching of the ventricular wall.

24 Claims, 10 Drawing Sheets

U.S. PATENT DOCUMENTS

| | | |
|---|---|---|
| 4,662,598 A | 5/1987 | Weingarten |
| 4,685,446 A | 8/1987 | Choy et al. |
| 4,685,447 A | 8/1987 | Iversen |
| 4,731,076 A | 3/1988 | Noon |
| 4,771,765 A | 9/1988 | Choy |
| 4,809,676 A | 3/1989 | Freeman |
| 4,820,303 A | 4/1989 | Brauman |
| 4,840,940 A | 6/1989 | Sottiurai |
| 4,861,330 A | 8/1989 | Voss |
| 4,902,273 A * | 2/1990 | Choy et al. ............... 600/18 |
| 4,938,766 A | 7/1990 | Jarvik |
| 4,969,864 A | 11/1990 | Schwarzmann et al. |
| 4,994,078 A | 2/1991 | Jarvik |
| 4,995,857 A | 2/1991 | Arnold |
| 5,005,591 A | 4/1991 | Austad |
| 5,092,879 A | 3/1992 | Jarvik |
| 5,139,517 A | 8/1992 | Corral |
| 5,169,378 A | 12/1992 | Figuera |
| 5,176,619 A | 1/1993 | Segalowitz |
| 5,192,314 A | 3/1993 | Daskalakis |
| 5,222,980 A | 6/1993 | Gealow |
| 5,267,940 A | 12/1993 | Moulder |
| 5,273,518 A | 12/1993 | Lee |
| 5,344,385 A | 9/1994 | Buck |
| 5,429,584 A | 7/1995 | Chiu |
| 5,653,676 A | 8/1997 | Buck |
| 5,655,548 A | 8/1997 | Nelson |
| 5,701,919 A | 12/1997 | Buck |
| 5,810,708 A | 9/1998 | Woodard |
| 5,824,071 A | 10/1998 | Nelson et al. |
| 5,888,186 A | 3/1999 | Trumble |
| 5,980,448 A | 11/1999 | Heilman |
| 5,984,857 A | 11/1999 | Buck et al. |

* cited by examiner

VENTRICULAR-ASSIST METHOD AND APPARATUS

FIELD OF THE INVENTION

The present invention relates to a ventricular-assist method and apparatus and, more particularly, to a ventricular-assist device (VAD) which can assist especially a failing heart and delay the development of end-stage heart failure and the point at which a heart transplant may be required. The invention also relates to a method of sustaining the failing heart utilizing a ventricular-assist device and an algorithm for operating a ventricular-assist device.

BACKGROUND OF THE INVENTION

The normal cardiac output, normalized by total body surface, is around 3.5 liter per minute per one square meter ($1/min/m^2$). In general, cardiac assist is necessary whenever a patient's cardiac output drops below the adequate blood supply needed to sustain proper blood perfusion, which is 1.8–23 $1/min/m^2$. Failure to supply adequate flow is defined as "systolic failure". However, more than 50% of the patients over 60 display inadequate ventricle filling and tissue congestion, which is defined as "diastolic failure". Cardiac assist is used to treat patients suffering from heart failure at a stage where conventional drug therapy proves ineffective.

Congestive Heart Failure (CHF) is a chronic disorder that develops over time, manifested clinically by an enlarged heart and symptoms and signs of low cardiac output and tissue congestion. The low cardiac output leads to decreased blood perfusion to vital organs (liver, kidney and brain). The CHF is also characterized by lung congestion (recurrent pulmonary edema) which threatens life and requires hospitalization. CHF is associated with profound symptoms that limit daily activities, is a debilitating disease with poor quality of life. CHF is the most common cause of hospitalization of patients over 60 years of age.

CHF has various etiologies, including cardiovascular disease (diseases which affect blood flow to the myocard), chronic hypertension (high blood pressure), incompetent values, inflammation of the heart muscle or the valves, substance accumulation (amyloid) and congenital heart problems.

Cardiovascular diseases (CVD) represent the leading cause of death in the industrialized world. CVD claimed 960,592 lives in the US in 1995 (41.5% of all deaths for that year). According to the US National Heart Lung and Blood Institute (NHLBI) and the American Heart Association there are approximately 5 million patients who suffer from Congestive Heart Failure (CHF) in the US and between 400,000 and 500,000 newly diagnosed patients each year. Long-term survival rates are low and the 5 year mortality rate for patients with CHF is 75% in men and 62% in women, while in patients with decompensated heart failure the mortality rate is 60% per year.

Patients suffering from Congestive Heart Failure (CHF) are initially treated with medication. While conventional drug therapy may delay the progress of CHF, it is not curative. Cardiologic intervention (such as Angioplasty and Stenting), surgery (Heart by-pass surgery, Cardiomyoplasty, Partial Ventriculectomy known as Batista's procedure), and mechanical devices are often considered when drug therapies prove ineffective or inadequate. Electrical disturbances of the heart that threaten or impair the quality of the patient's life have been treated effectively with pacemakers and implantable defibrillators. However, congestive heart failure has not been addressed effectively. Currently, the only available method of treating end-stage CHF is a heart transplant.

The demand for temporary and permanent cardiac-assist devices is remarkably large; in 1993 between 40,000 to 70,000 patients needed life-sustaining assist devices or a total artificial heart, and an additional 80,000 to 200,00 patients needed quality of life improvements by surgery (Cardiomyoplasty or Heart Booster).

Ventricular-assist devices are needed for:

Bridge-to-Recovery—cardiac assist for patients whose heart has sustained serious injury, but can recover if adequately supported. This includes the use of a cardiac-assist device after surgery in order to provide support until the heart regains its ability to pump. Temporary cardiac support is intended primarily to prevent or reduce damage from cardiac failure or to support adequate blood circulation.

Bridge-to-Transplantation—patients awaiting heart transplants and who are not scheduled and when the heart failure is unresponsive to medical treatment.

Existing temporary mechanical cardiac devices are divided into three groups:

1. Temporary cardiac assist for several hours, as the intra-aortic balloon that is frequently utilized for patients with heart failure after open-heart surgery due to failure to wean from the cardiopulmonary bypass.

2. Long-term (days, weeks, months) Ventricular Assist Device (VAD), as a bridge to heart transplantation.

3. Permanent support by Total Artificial Heart (TAH).

Intra Aortic Balloon Pump (ABP). The IABP has been in clinical use for over 20 years. The IABP consists of a balloon (30–50 ml) that is inserted into the descending aorta and is inflated during the diastole and deflated during the systole. The IAB increases the cardiac output by less than 0.5 $1/min/m^2$.

Consequently, although it was designed to assist a failing heart by improving blood perfusion, it requires a certain threshold level of cardiac output and cannot take over the pumping function of the heart. As a result, it can only be utilized in treatment of patients who require mild levels of mechanical assistance (unless there is a supplemental assisting heart device). The device reduces the energy consumption and allows the heart to recover. However, the IABP is used only for short-term circulatory assist due to high risk of severe thromboembolic complications.

Ventricular Assist Devices (VAD)—VADs take over the complete pumping function of one or both sides of a failing heart. They unload the assisted ventricle. Left Ventricular Assist Devices have been approved for use by the FDA as bridge-to-heart transplantation, to keep patients alive who are awaiting a donor heart. These devices have also been approved for use by patients whose hearts are in failure but may be able to recover by reducing the myocardial work (unloading), including patients in post-surgical life-threatening heart failure.

More than a dozen companies (listed below) are developing devices, ranging from left-ventricular assist products to total artificial hearts, that offer CHF patients either longer-term support with an alleviation of symptoms, and/or an alternative to heart transplant. Some of these (Thermo CardioSystems, Thortec, Abiomed and Baxter Healthcare) have ventricular assist products on the U.S. market. Ventricular-assist devices are generally employed on a temporary basis, with treatment periods ranging from a few hours to a few weeks, or at most, a limited number of months. However, some devices have been designed for long-term use and can be considered lifetime support systems. To date, such lifetime support is still in developmental and experimental stages and was not approved by the FDA.

There are five major types of VAD: Roller pumps, Centrifugal pumps, Pneumatic devices, Electrical devices and direct mechanical actuators. These devices differ in the design, indications and duration.

Roller and Centrifugal Pumps are approved for short-term (i.e. hours) support of patients undergoing heart surgery. These devices generate a non-pulsatile blood flow which severely restricts the time patients can safely remain on support. They also require additional medical personnel to provide constant monitoring and ensure that the pump is operating correctly.

Transplant bridging, and possibly long-term cardiac assistance may also be accomplished with implantable axial flow and centrifugal pumps. Examples of companies pursuing cardiac-pumping technology include: Jarvik Research, Medtronic Inc., 3M Corporation Inc., Kirton Medical, Micromed Technology and Cardiac Assist Technologies.

A high-speed pump has been developed recently by Micromed in co-development with the National Aeronautics and Space Administration (NASA). This miniaturized DeBakey/Ventricular Assist Device (30 mm×76 mm) weighs only 93 grams, making it about one-tenth the size of portable heart-assist devices already on the market.

The pneumatic devices were the first to be approved for clinical use. Through December 1997 the BVS 5000, developed and manufactured by Abiomed Inc. was the only approved product, and it is the only device that can provide full circulatory assistance approved by the US FDA as a bridge-to-recovery device for the treatment of reversible heart failure. The BVS-5000 (BVS) is a pneumatic extra-corporeal, bi-ventricular assist device, allowing the heart to rest, heat and recover its function. However, the blood circulates out of the body and the patient cannot be ambulatory. The company's first full year of marketing the BVS in the U.S. was 1994.

Thoratec Laboratories Corporation has developed an implantable pneumatic-assist device, which is connected to an external drive by a percutaneous air-drive line. This system was also approved by the FDA as a bridge to heart transplant.

The electrical VAD will ultimately be completely implantable with an implantable controller, battery and charger (secondary coil). The main electrical pulsatile implantable pump are: Novacor N-100 (Baxter Healthcare Corp.), Heartmate 1000 NE LVAS (ThermoCardioSystem Inc.) and Pennsylvania State University System.

In September 1998, the first two ambulatory implantable left ventricular-assist systems (LVAS), from Baxter and ThermoCardioSystem Inc (TCS), were approved in the U.S. TCS' implantable electric HeartMate LVAS has been marketed since 1994. In Europe, the Baxter Novacor LVAS has been approved as a commercial product since 1994. These devices represent a significant advance over first-generation technology, since they allow patients to live outside the hospital while awaiting transplantation. The Baxter Novacor is an electromechanical pump that is implanted in a patient's abdomen and connected to the left ventricle of the heart. The system is operated by an external, portable electronic controller, and is powered by battery packs, which the patient typically wears around the waist in a shoulder vest or backpack. Nearly 900 patients worldwide have received the Novacor LVAS: two patients have currently been supported for more than three years by their original devices. In Europe, the device has helped to rehabilitate more than 20 patients' hearts to the extent that neither VAD assistance, nor heart transplant is necessary.

The Direct Mechanical Actuator is a different approach, taken by Cardio Technologies. This company is pursuing a cuff-like device that is placed around the outside of the heart. This device applies external pressure to enhance blood flow. A somewhat similar device, designed to reduce the size of an enlarged heart, is under development by Acorn Cardiovascular. Abiomed is also in early development stages of the Heart Booster system designed to wrap around the heart to provide ventricular augmentation.

Three additional surgical methods have been developed recently as alternative to cardiac assist, in order to improve the residual cardiac function: 1) Dynamic Cardiomyoplasty; 2) Partial Ventriculectomy or Batista operation, and 3) Percutaneous transmyocardial revascularization (PTMR). However, these methods are controversial.

In the Dynamic Cardiomyoplasty technique, a surgeon wraps some of the patient's skeletal muscle around the weakened heart and stimulates the repositioned muscle to synchronously squeeze the heart during diastole. Dynamic Cardiomyoplasty is highly invasive and involves complicated surgical procedures. Medtronic is also involved in clinical studies of this pacemaker-aided technique using the latissimus dorsi muscle.

Percutaneous transmyocardial revascularization (PTMR) is a recently approved catheter-based laser technique that involves drilling about 50 tiny holes in the left ventricle to improve blood flow to the heart muscle. The laser surgery offers a cost-effective alternative to transplantation for certain patients with severe angina, who were not candidates for angioplasty or bypass surgery. The precise mechanism underlying this approach is controversial.

OBJECTS OF THE INVENTION

It is the principal object of the present invention to provide an improved ventricular-assist device that is free from the drawbacks of earlier devices, is especially effective in assisting a failing heart and in some cases may even be able to improve the cardiac function of the natural tissue of a failing heart.

It is also an object of the invention to provide an improved method of assisting a failing heart.

Still a further object of the invention is to provide a method of and an apparatus for ventricular assistance whereby drawbacks of earlier systems can be avoided, the assistance provided can be more reliable and the energy drain on the assisted heart can be minimized.

SUMMARY OF THE INVENTION

These objects are attained, in accordance with the invention in a ventricular-assist method which comprises:

(a) inserting into the failing ventricular cavity (left, right or both) of a failing heart through a wall thereof a respective expandable intraventricular chamber having a maximum volume of 30 ml;

(b) in cadence with normal functioning of the failing heart, effecting expansion of the respective intraventricular chamber with each heart beat and commencing only after opening of an outlet valve of the respective ventricular cavity of the failing heart or only after a detected shortening of a monitored region of a wall of the respective ventricular cavity of the failing heart and continuing during an ejection phase of the respective ventricular cavity, thereby augmenting ejection volume from the respective ventricular cavity by up a maximum volume of the intraventricular chamber per systolic phase;

(c) controlling a time course of expansion of each intraventricular chamber in step (b) to reduce a shortening of a respective ventricular wall of the failing heart by comparison with ventricular wall shortening prior to insertion of the respective intraventricular; and (d) depressurizing and contracting each the intraventricular chamber immediately upon closing of a respective outlet valve of the failing heart.

The method of the invention further comprises the steps of:

measuring ventricular wall motion during expansion of a respective intraventricular chamber in step (b); and controlling a profile of the expanding intraventricular chamber in a course of expansion thereof to decrease the measured ventricular wall motion thereby obtaining an increase in the pressure within the respective cavity and increase the cardiac output.

According to the invention, at least one parameter of ventricular wall shortening and at least one parameter of ventricle output can be measured during systole and in response to measurement of these parameters, selectively either in real time or by beat-by-beat computation, and a designed shape for each interventricular chamber is determined and the shape and a rate of expansion and contraction of the interventricular chamber are controlled to correspond to the desired shape.

The parameters of wall shortening which can be monitored are the ventricular diameter, ventricular volume, and ventricular wall strain or the ventricular flow in preferred embodiments of the invention. The interventricular chamber is preferably a balloon with computer-controlled expansion and implanted in either interventricular cavity or both interventricular cavities.

In terms of the apparatus, the system can comprise the steps of:

(a) inserting a failing ventricular cavity (left, right or both) of a failing heart through a wall thereof a respective expandable intraventricular chamber having a maximum volume of 30 ml;

(b) in cadence with normal functioning of the failing heart, effecting expansion of the intraventricular chamber with each heart beat and commencing only after opening of an outlet valve of the respective ventricular cavity of the failing heart or only after a detected shortening of a monitored region of a wall of the respective ventricular cavity of the failing heart and continuing during an ejection phase of the respective ventricular cavity, thereby augmenting ejection volume from the respective ventricular cavity by up a maximum volume of the intraventricular chamber per systolic phase;

(c) controlling a course of expansion of each the intraventricular chamber in step (b) to reduce a shortening of a respective ventricular wall of the failing heart by comparison with ventricular wall shortening prior to insertion of the respective intraventricular; and (d) depressurizing and contracting each the intraventricular chamber immediately upon closing of a respective outlet valve of the failing heart.

The apparatus can have a computer receiving input from the sensor and controlling the actuator with an output, the computer being programmed for each heartbeat (n) to:

(a) evaluate cardiac output and work at the n beat;

(b) compare the evaluated cardiac output and work at the n beat with a desired cardiac output to determine an amplification factor ($A_F$);

(c) multiplying the amplification factor ($A_F$) by a weighting function (W(t)) as determined by an operator to generate a magnitude of a feedback loop;

(d) evaluate ventricle wall shortening ($S_n(t)$) and compare the evaluated wall shortening with a desired wall shortening (Des(t)) to obtain a difference $Err_n(t)=Des(t)-S_n(t)$;

(e) generate an expansion function $EXP_{n+1}(t)=EXP_n(t)+A_F*W(t)*Err_n(t)$; and (f) control expansion of the intraventricular chamber at a next beat (n+1) with the expansion function $EXP_{n+1}(t)=EXP_n(t)+A_F*W(t)*Err_n(t)$.

Advantageously the computer is a computer which controls the intraventricular chamber at the next beat (n+1) with the expansion function by regulating onset time of expansion and the function of expansion.

The amplification factor ($A_F$) is multiplied by a weighting factor (W(t)) at each beat where $0 \leq W(t) \leq 1$ and $0 \leq t \leq T$, and t=0 is the onset of expansion and t=T is the end of expansion.

The computer can receive input from the sensor and can control the actuator with an output, the computer being programmed for each heartbeat (n) to:

(a) evaluate cardiac output and work at the n beat;

(b) compare the evaluated cardiac output and work at the n beat with a desired cardiac output and determine an amplification factor that will not cause wall stretch in part based upon additional inputs;

(c) evaluate ventricle wall shortening ($S_n(t)$) at the n beat and providing the ventricle wall shortening as one of the additional inputs;

(d) detect possible ventricle wall lengthening from the evaluation of the wall shortening in step (c) and providing therewith another of the additional inputs, and triggering an alarm upon ventricular wall lengthening (f) from the amplification factor and a desired profile of expansion, determine a time course of expansion of the intraventricular chamber; and (g) generate an expansion function representing the time course of expansion control of the intraventricular chamber at a next beat (n+1) with the expansion function.

The means for detecting a state of the outlet valve can include at least one of the following:

means for measuring intraventricular and aortic pressure or a gradient between intraventricular and aortic pressure;

a Doppler or an ultrasonic or electromagnetic flowmeter measuring ventricle outlet flow;

ultrasound or electrical impedance means for measuring intraventricular volume;

strain gauge means for measuring ventricle wall shortening; and means for detecting heart sounds.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
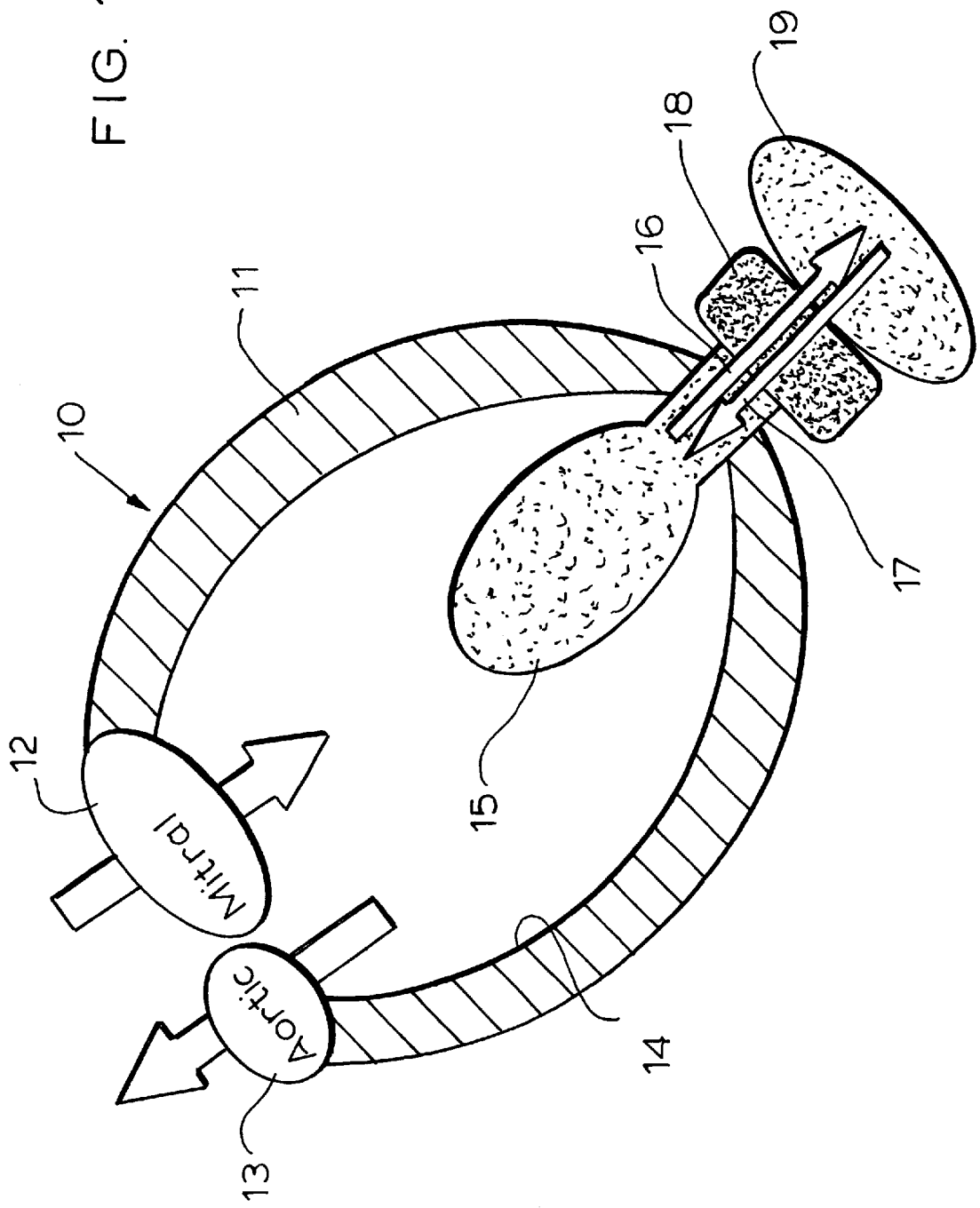
FIG. 1 is a diagram illustrating the use of the ventricular-assist device in a left ventricle of a failing heart.

In FIG. 1 the left ventricle 10 of a failing heart has been shown and comprises the ventricle wall 11, the inlet for mitral valve 12 and the outlet or aortic valve 13. Within the ventricle cavity 14 an intraventricular chamber is provided in the form of a balloon 15 which can be expanded and contracted by the flow of physiological liquid, for example, in the direction of arrows 16 and 17 from actuator 18. The extraventricular chamber is represented at 19. The fluid moves back and forth from chamber 19 to chamber 15 as controlled by the actuator 18. Thus the VAD of the invention consists of two chambers, the ventricular chamber or balloon (IVC) and the extraventricular chamber 19. The device of the invention is not intended to replace the entire function of the failing heart but merely to add additional cardiac output, thereby increasing the low level natural cardiac output of around 2.5 liters per minute by up to, say, two liters per minute. An added stroke volume of less than 30 ml/beat is provided at a heart rate of about 70 per minute and hence the volume of the intraventricular chamber 15 can be less than 30 ml. The VAD improves the systolic function of the ventricle and hence the ability of the heart to eject fluid. The improved systolic function and the increase in the systolic pressure are mediated by changing the loading condition imposed on the ventricle wall.

The increase in the ejected volume results from an increase in the left ventricular LV pressure and the combined contribution of the intraventricular chamber. (IVC) expansion and the physiological heart shortening. This VAD improves the LV filling (diastolic function) by imposing rapid cardiac wall shortening during early relaxation, which causes rapid deactivation of the LV and increases the LV compliance.

During systole the device produces less than 1.6 watts of external work and the average (systole and diastole) power is less than 0.5 watts. Consequently, from heat and energy considerations, with reasonable electromechanical efficiency a device based on the suggested mode of operation can be implanted inside the thorax, and energized by an implanted battery or other prime mover.

To summarize, the main concepts are:

(a) Insertion of an intraventricular chamber (IVC)/balloon, into the ventricle cavity.

(b) Control of the appropriate timing of the device inflation and deflation.

(c) Control of the appropriate volume and profile of inflation/deflation.

(d) Perform the above (b) and (c) in such a way that it will not deteriorate the work of the ventricle during systole and will not increase its energy consumption.

(e) Perform the above (b) and (c) so that most of the added external work will turn into work done on the blood.

(f) Perform (b) and (c) in such a way that it will improve the ventricle compliance and coronary perfusion, during diastole.

To understand the mode of operation and the significance of the appropriate triggering, some brief summary of the mechanical function of the physiological heart is required.

Systolic Function

1. The external power generated by a normal heart, when the systolic pressure is 120 mm Hg, ejected volume is 70 ml, and systolic duration is 0.2 sec, is only 5.5 watts (during systole).

2. To increase the ejected volume by 20 ml against a systolic pressure of 120 mm Hg, during the systole—the needed power is only 1.6 watts.

3. Muscle shortening and left ventricle compression (as done by Direct Mechanical Ventricular Assistance) decreases the average force generated by the actin-myosin crossbridges (Xbs), the motor units of the muscle.

4. Left ventricle expansion during systole (eccentric work) deteriorates LV function, so does small vibrations.

5. The decrease in muscle shortening increases the time over which the Xbs are at a strong force-generating state (increases the duty cycle of the force-generating motors).

6. The energy consumption by the sarcomere (the muscle contractile element) increases with the increase in the shortening velocity, at high activation (free calcium level).

Diastolic Function

7. Significant number of failing hearts (more than 50% at old age)—suffer from diastolic failure, i.e. failure in filling the left ventricle chamber.

8. The decrease in the LV compliance at early diastole, the decrease in the early filling is partially attributed to a decrease in the rate of muscle relaxation (impaired calcium dissociation from the regulatory proteins).

9. Muscle shortening during the isovolumic relaxation period—causes rapid force decrease and deactivation (decreases the bound calcium) and increases muscle (ventricle) compliance.

10. An improvement in ventricle loading conditions, and particularly the preload (unloading) may cause long-term muscle remodeling and significant restoration of the normal function (e.g. LV remodeling after mitral valve replacement and after prolonged unloading by the ventricular-assist device).

Note that the above features of the physiological heart imply that the control of an intraventricular device cannot rely only on the electrical activity, aortic pressure or heart sound but should be based on ventricle mechanics, i.e. ventricle diameters/volume or wall strains and on the timing of aortic valve opening and closure.

This VAD is designed so that it will utilize the physiological features of the biological heart mechanics (specifically items #3, 4, 5, 9, 10—above).

1. The device consists of two chambers, an Intra-Ventricular (IVC) and extra-cardiac chamber. The volume of the intra-cardiac chamber is less than 30 ml.

2. This VAD improves systolic function and increases the external work done by the LV by changing the LV pressure-volume loop (FIG. 3), it increases:
   (a) The pressure generated by the LV wall.
   (b) The ejected volume.

3. The increase in the systolic pressure is achieved by imposing almost an isovolumic regime on the LV wall (phase BC) and decreasing the LV wall shortening.

4. The increase in the ejected volume results from:
   to (a) An increase in the LV pressure.
   (b) Combined contribution of the intraventricular chamber (IVC) expansion and the LV wall shortening.

5. The above is achieved by timing the IVC expansion after the opening of the aortic valve. Moreover, the maximum effect will be achieved if the rate of IVC expansion is maximal early in the ejection phase, when the ventricle flow is maximal (Note FIGS. 4 and 10).

6. The LA-VAD improves the LV diastolic function and LV filling by:
   (a) Producing rapid emptying of the LV (phases CDA in FIG. 3) and decreasing the LV volume.
   (b) Increasing the LV wall compliance, due to the imposed LV wall shortening during the early relaxation phase (phase CD).

7. The IVC deflation/compression should start after the closure of the aortic valve, but as early as possible during the isovolumetric relaxation phase.

8. The LV diameters, epicardial strains or ventricle volume are monitored in order to regulate the profile of the IVC expansion, to avoid ventricle stretching (eccentric work).

The average external power (P) needed in order to increase the cardiac output ($\Delta CO$) by half a liter per minute while the systolic pressure ($P_{SYS}$) is about 120 mm Hg is only 0.14 watts of mechanic power. Since:

$$P = 1/456 \cdot \Delta CO \cdot P_{SYS} \quad \text{(watts)}$$

where $P_{SYS}$ is measured in (mm Hg) and $\Delta CO$ in (liter/min).

Consequently, from heat and energy considerations, a device with reasonable electromechanical efficiency can be implanted intrathoracic, and energized by an implanted battery.

Figure 3:
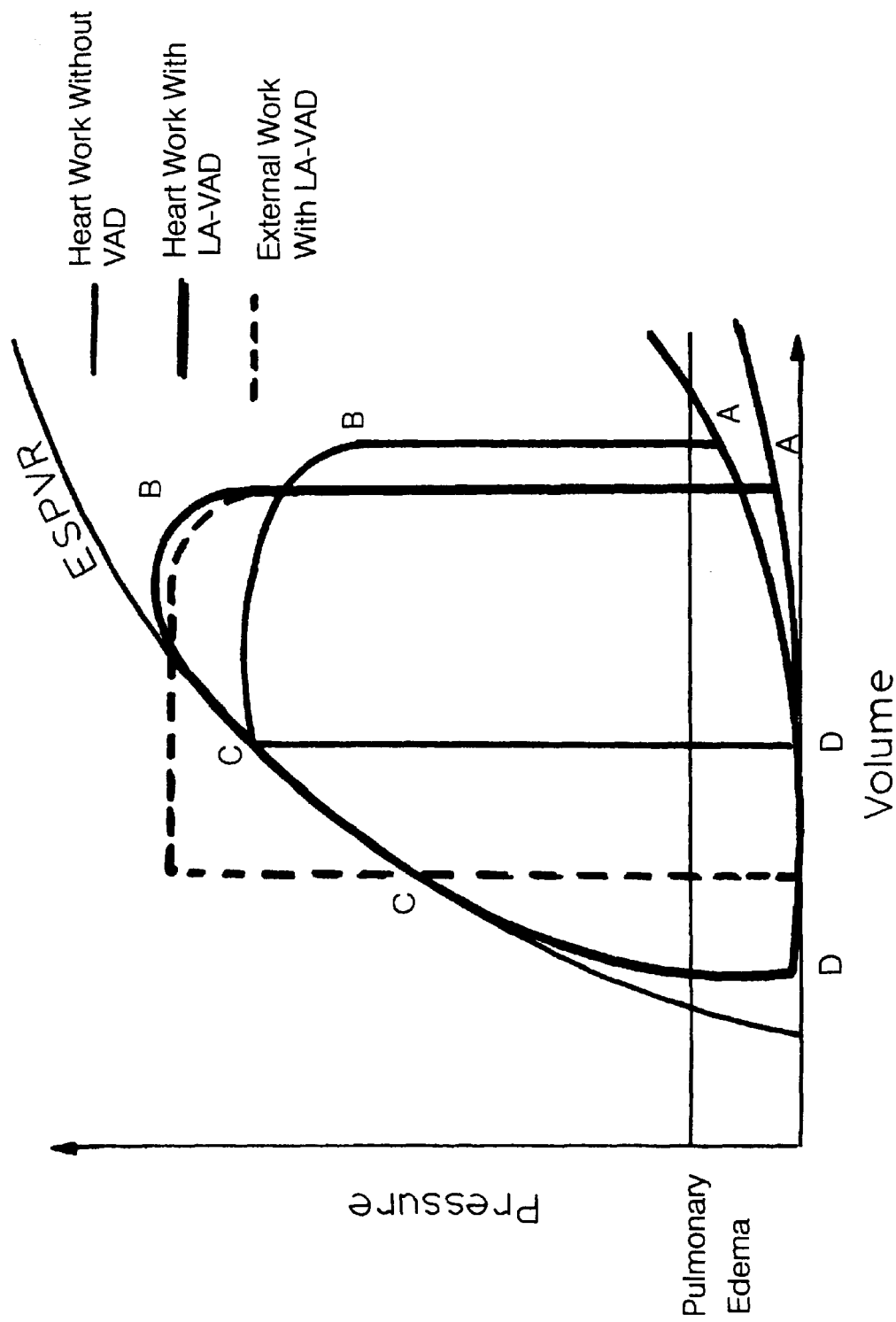
FIG. 3 is a pressure/volume graph illustrating the pressure-volume loop of a failing heart and with the ventricular-assist device of the invention.

In FIG. 3, the pressure volume loop of the failing heart has been shown in thicker lines with the ventricular-assist device and with a thinner line without the ventricular-assist device. The loops represent the work done by the ventricle and there is an additional increase in the external work done on the blood when the assist device is working as represented by the broken line.

Figure 4:
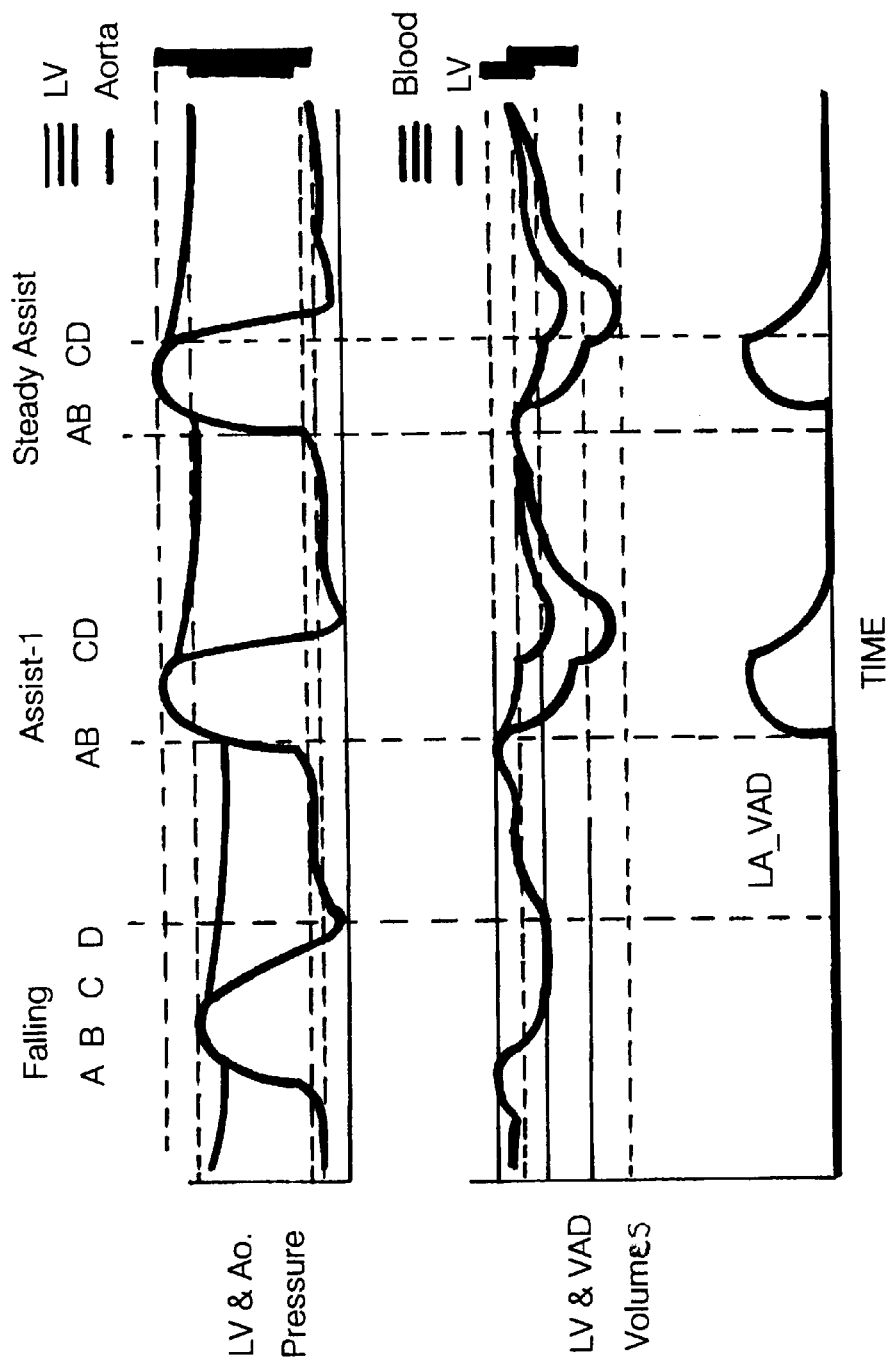
FIG. 4 is a diagram showing the time course of inflation and deflation of the intraventricular chamber.

FIG. 4 shows the time course of inflation and deflation of the intraventricular chamber of the VAD. This diagram also shows the effects on left ventricle pressure, aortic pressure, left ventricle wall motion and the changes in intraventricular blood volume.

Figure 2:
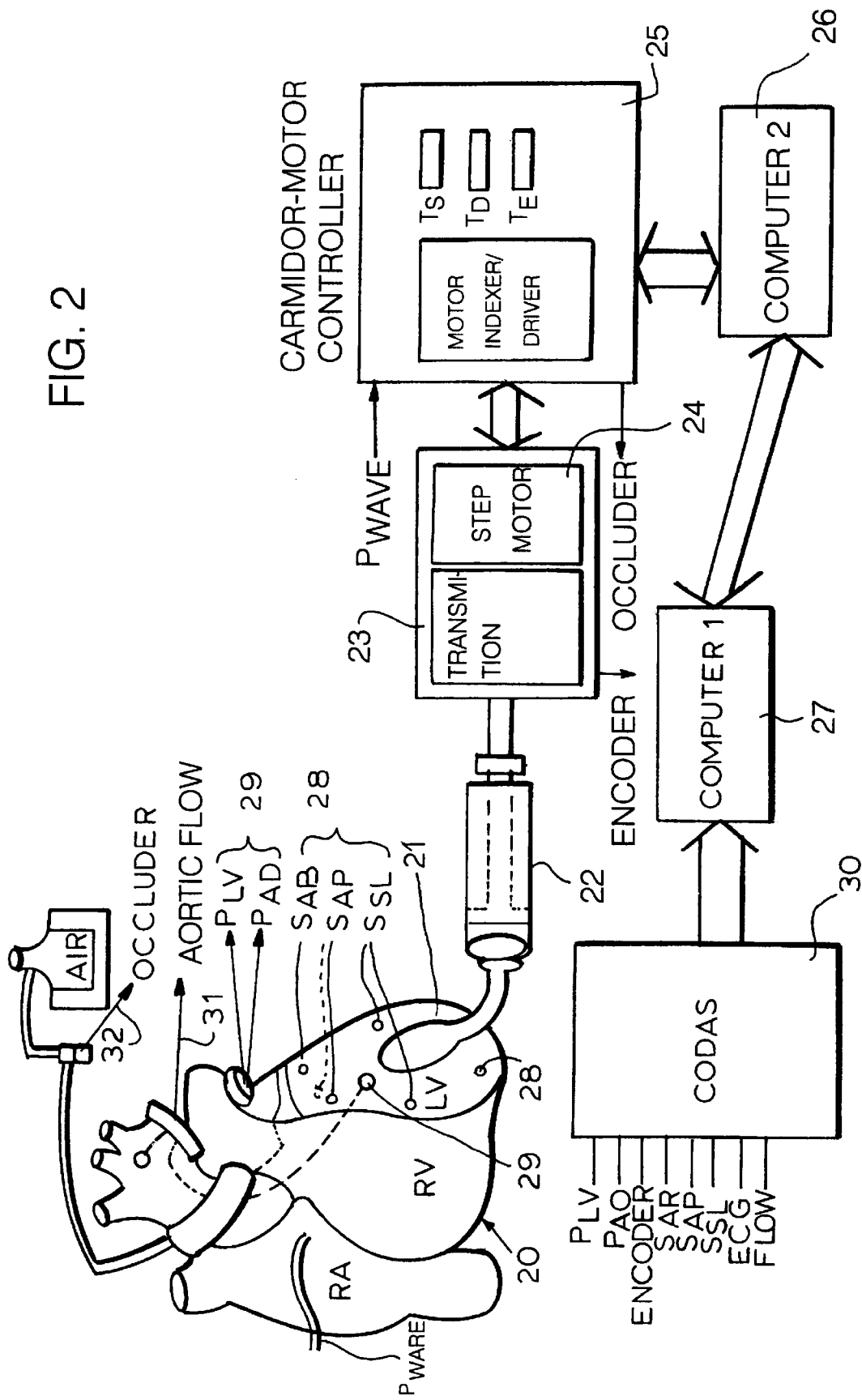
FIG. 2 is an apparatus as used in the feasibility study of the invention, applied to pigs.

FIG. 2 shows the setup with respect to a heart in a feasibility study but is applicable to an embodiment applied to a failing heart with the exception that fewer sensors may be required. The heart is represented at 20 and the right atrium is labeled at RA, the right ventricle at RV and the left ventricle at LV. The left ventricle contains the VAD 21 which is here expanded and contracted with a syringe pump 22 driven by the transmission 23 from a stepping motor 24 of a motor controller 25 operated by the computer 26, i.e. the motor-control computer. A computer 27 analysis the data from the sonomicrometers (ultrasound crystals) 28, pressure transducers 29 and flow meter 31. The position of the pump 22 is fed to the encoder input and represents the degree of expansion of the VAD. Data acquisition system 30 is used to sample the sensor and transducer inputs to the computer 1.

Figure 5:
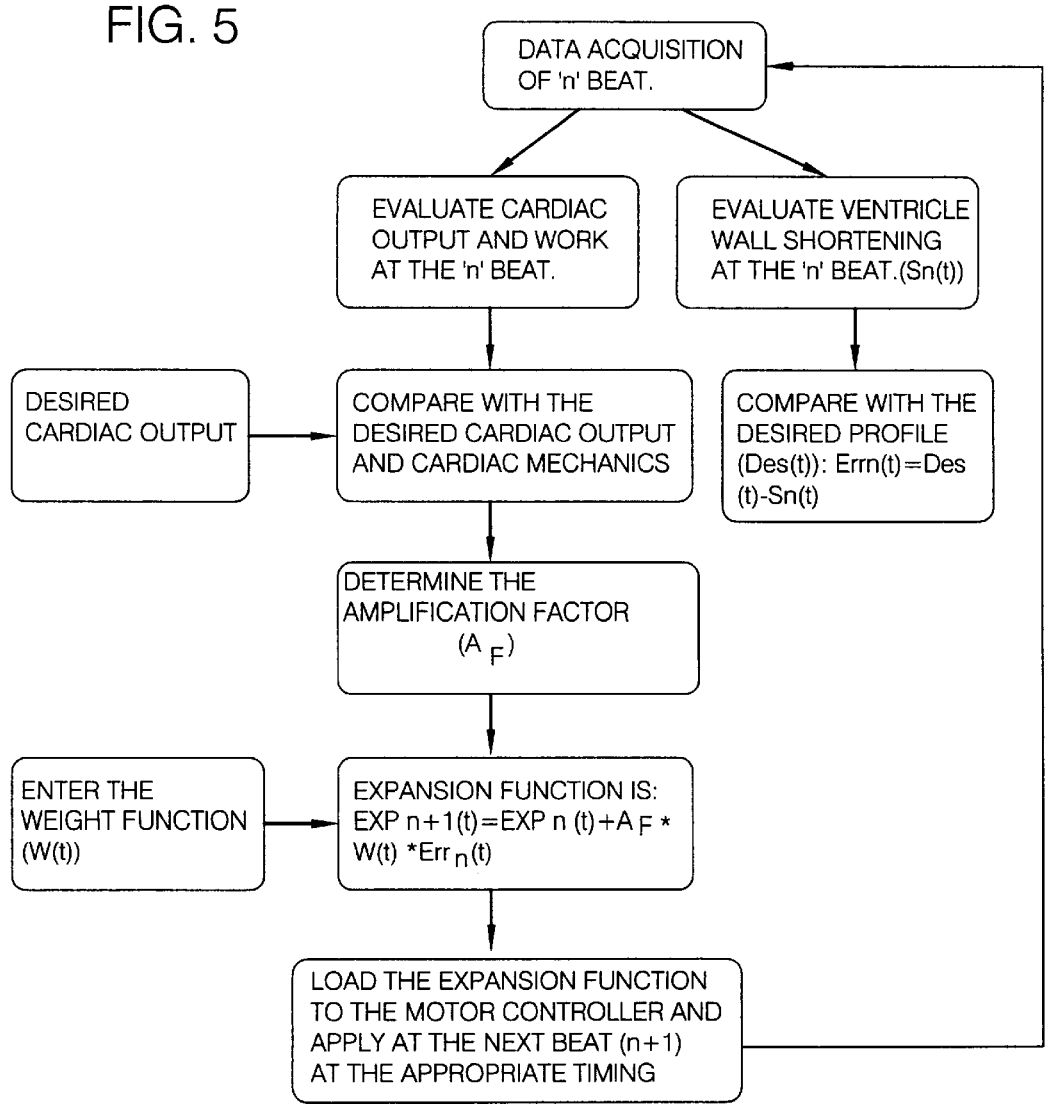
FIG. 5 is a flow diagram of one algorithm for the automatic regulation of expansion of the intraventricular chamber based upon characteristics of ventricle wall shortening.
Figure 6:
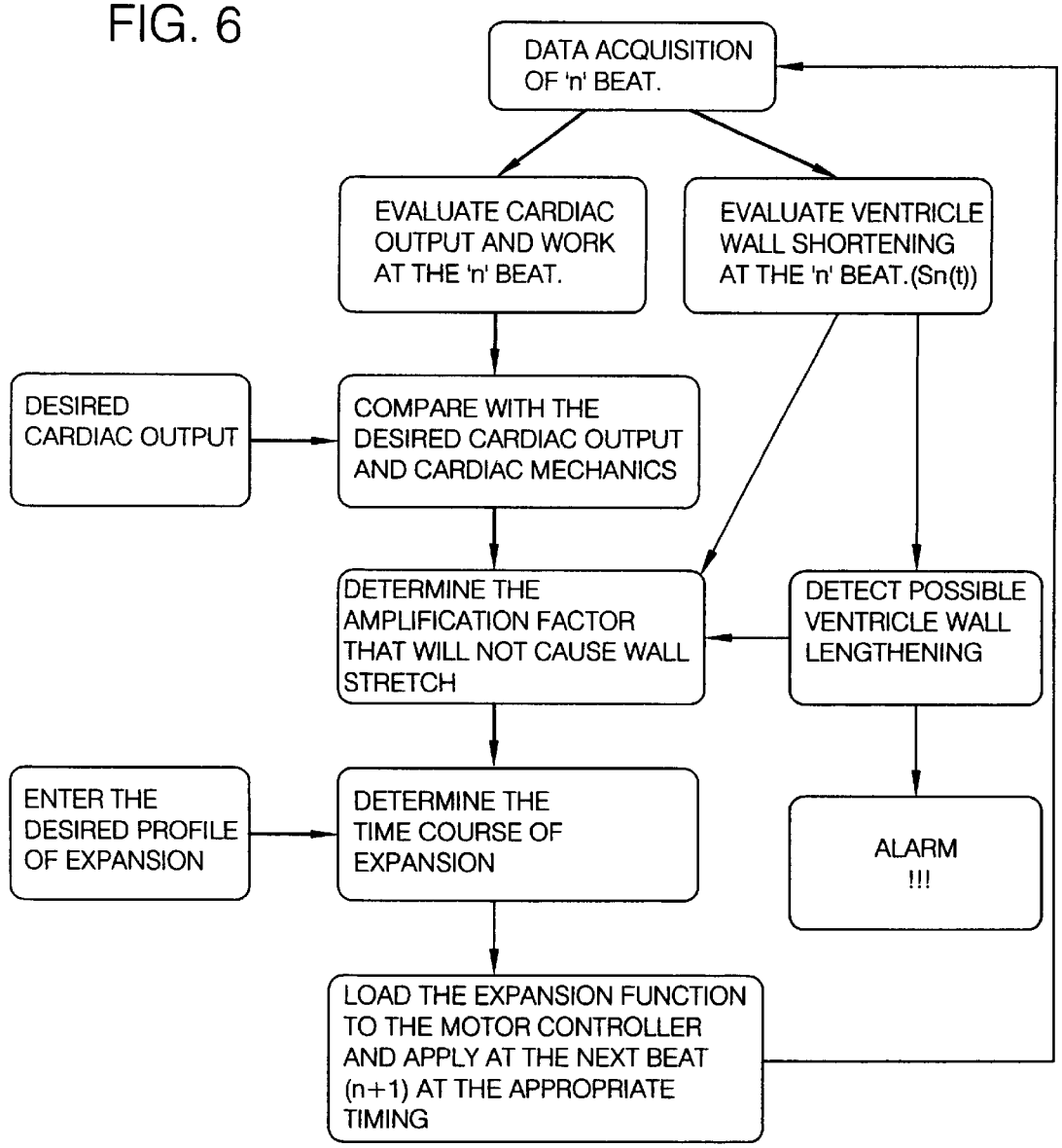
FIG. 6 is a similar diagram for a semiautomatic mode of operation.

Thus possible algorithms for controlling the profile of expansion of the ventricular chamber have been shown in FIGS. 5 and 6. FIG. 5, in particular, represents a flow chart for an automatic mode of regulation of the intraventricular chamber expansion with the profile during expansion being based upon characteristics of the ventricle wall shortening.

FIG. 6 is a flow chart for regulating expansion where a profile is determined manually but in conjunction with continuous control so that the ventricle wall function will not deteriorate.

The overall algorithm for increasing the cardiac output is not based, therefore, merely on a control of ventricle cavity volume but on control of ventricle cavity pressure and the shape and rate of expansion and contraction of the IVC.

The device is designed to improve the ventricle wall capability to generate sustained elevated pressure. The intraventricular chamber expansion aims not just to push blood out of the ventricle but to control the pressure generated inside the ventricle cavity, which is maintained by the ventricle wall. To increase the ventricle ejected blood volume it is required to increase the pressure inside the ventricle cavity at any given impedance of the circulatory system, since the cardiac outflow is determined by the ventricle pressure and the peripheral circulatory impedance. The maximal pressure that the ventricle it wall can generate is obtained when the ventricle does not shorten. Ventricle wall shortening decreases the generated pressure (which relates mainly to the phenomena denoted as the force-velocity relationship). Therefore, the IVC expansion is used to diminish the ventricle wall shortening, which allows increase of the ventricle wall stresses and the generated ventricle pressure. Consequently, part of the volume expansion of the intraventricular chamber is used to compensate for the diminished ventricle wall shortening, while the rest is added to the ventricle outflow.

However, the IVC expansion is limited so that it will not cause ventricle wall stretching. Stretching the muscle before the electrical stimulation or during the contraction (eccentric work) damages the cytoskeleton of the muscle—and leads to cell death (apoptosis) which leads to gradual deterioration of the muscle ability to generate force and increases its resting force or stiffness. Consequently, inappropriate control of IVC expansion leads to reduction of the generated pressure during the systole and impaired filling of the ventricle during diastole.

To achieve the maximal generated pressure, the expansion of the intraventricular device is controlled so that ventricle shortening will be minimized. This can be done in real time, when the measurements of the ventricle wall motion are inversely fed back to the intraventricular device controller, or by beat-to-beat regulation (see FIGS. 5 and 6). In the beat-to-beat regulation the parameters of ventricle shortening are inversely fed into the IVC controller after multiplication by an amplification factor (A,) (FIG. 5). This diminishes ventricle wall shortening. However, the exact effect cannot be predicted since the ventricle wall function is complex (nonlinear), time varying and spatially inhomogeneous). Therefore, the algorithm is based on successive iterations that gradually decrease the ventricle wall shortening, but allow higher cavity pressure while the added outflow is provided by the IVC (FIG. 5). The obtained measured parameters during the next beat are fed (inversely and after amplification/attenuation) again and are used to correct the first approximated profile of the IVC expansion. After few iterations (less than 10, or 10 seconds from the starting to operation) the desired profiled of IVC expansion is achieved.

This method allows continuous modification of the IVC function at almost real time, during its long-term operation, at various heart rate and physical activities (that change the loading condition imposed on the heart).

The beat-by-beat adaptive control is the preferred mode of operation (over the real time method) since it is fast enough (correction within a few beats) and it prevents high frequency oscillation. The real time method, where the IVC expansion is determined within a single beat carries the hazard of causing fluctuation in the rate of expansion which will deteriorate the ventricle wall function. (The ventricle wall is sensitive to oscillation/vibration in the loading conditions).

In most practical expected operations the IVC will not operate at maximal power, as defined above, but will only a partially diminish ventricular shortening. The aim is to add the minimal required eternal work that will allow substantial improvement of the quality of life. Note that normal cardiac output is about 3.5 liter/min/mm$^2$ while cardiac output of less than 1.8 liter/min/mm$^2$ is incompatible with life and causes organ hypo-perfusion and death. (An aortic balloon provides less than 0.5 liter/min—and provides enough support in most (85%) cases of the postoperative cardiogenic shock). Similarly, we provide that the device should give an additional 1 liter/min, i.e. about 10–15 ml per beat. It is not desired to work at full power since under this condition the energy consumption of the ventricle will be maximal (the maximal energy consumption of the heart is at isovolumic contraction) and also the energy consumption of the device will be increased. Therefore the exact magnitude of IVC expansion is determined by the desired cardiac output. The parameters of the IVC expansion that are under control are:

a. Onset time of expansion.
b. Rate of expansion (initial rate and late rate of expansion).
c. Maximal volume.
d. Timing the end of expansion.

Onset time of expansion: The onset time of expansion is defined by the time onset of significant ventricular wall shortening of the monitored portion of the ventricle wall. For a homogeneous ventricular wall—the onset time is determined by the opening of the ventricle outlet valve. For an inhomogeneous ventricle wall structure, as in a case of ventricle aneurysm (where part of the cardiac muscle has died and was replaced by a fibrotic tissue) the onset time of the inflation may be determined by the performance of the preserved myocardium (cardiac wall tissue). The ventricle contraction and pressure generation cause bulging out of the aneurysmatic (fibrotic) portion of the ventricle wall and shortening of the preserved myocardium. The preserved myocardium is doing work on the aneurysmatic wall, while the aortic valve is still closed and without ejecting blood of the heart. In this case the IVC can expand before the opening of the ventricle outlet valve in order to compensate for the dilatation and bulging of the aneurysm wall. To enable this, the onset time of expansion is determined by monitoring the shortening of the preserved functional region of ventricle (the region of interest) and some of the sensors of the device are placed at the region of interest. (The sensors are described below). Therefore, the onset time may be determined by global parameters as the opening of the outlet valve and by regional parameters.

The rate of expansion and the time course of expansion may be determined explicitly by the algorithm defined in FIG. 5. However, there is some flexibility that allows modulation of the time course of expansion by making the amplification factor ($A_F$) a function of time ($A_F(t)$) and not a constant. The amplification factor ($A_F$) is multiplied at each iteration (beat) by the weighting function (W(t)) that is determined by the operator based on empirical observation (see below) and allows changing the magnitude of the feedback loop within the time of expansion. $0 \leq W(t) \leq 1$, where t varies between the time onset of expansion (0) and the end of expansion (T), $0 \leq t \leq T$. The default mode of operation is with constant weighting function (W(t)=1). However, the weighting function allows optimization of the IVC expansion based on the following idea: The rate of blood ejection from the normal and failing ventricle is maximal at the initial phase of the ejection phase, just immediately after the opening of the ventricle outlet valve. Consequently, the main contribution of the ventricle wall to the cardiac output is obtained at the early phase of ejection. The higher amplification factor at the early phase of expansion will diminish the contribution of the ventricle wall shortening to the cardiac output but will increase the cavity pressure. A higher amplification factor at the last phase of expansion allows the elongation of the duration of the ejection phase by allowing the ventricle wall to sustain pressure for a longer time. Hence, the weighting function allows regulation of:

the contribution of the ventricle wall to the cardiac output;
the maximal cavity pressure; and
the duration of the ejection phase.

The higher the magnitude of the feedback coefficient at the early phase of expansion, the lower is the contribution of the ventricle wall shortening to the cardiac output.

Moreover, the weighting function may be used for weaning the patient from the device. Decreasing the magnitude of the feedback loop at the early phase of ejection, i.e. decreasing the weighting function at the early phase of IVC expansion (W(t)=0 as t approaches 0), increases the contribution of the ventricle wall shortening to the cardiac output. The weighting function allows modulation of the work of the failing heart and allows gradual adaptation of the failing heart to normal loading conditions. It is expected that there will be a gradual decrease in the failing heart diameter when the assist device is working. Therefore, it is expected that the device will allow gradual decrease in the heart diameter and gradual recovery of its ability to generate almost normal cardiac output. Hence, the device can be used as a "bridge to recovery"—and after several months, it will be possible to remove the device without the need for cardiac transplantation. In that case, the heart has to be gradually accommodated to the prevailing loading condition with the device and the assistance of the device should be gradually attenuated.

The volume of the expansion of the intraventricular chamber is increased until the desired cardiac output is reached or until another limiting maximum is achieved. That limiting maximum can be the beginning of stretch in the ventricular wall. The total volume of the balloon is fixed as has been stated previously.

The end of expansion of the intraventricular chamber can be determined by cessation of ventricle shortening at a monitored region or occlusion of the ventricle outlet valve. Both are determined by appropriate sensors.

The algorithm allows operator intervention. The algorithm of either FIG. 5 or FIG. 6 provides monitoring of at least one parameter of ventricle motion to prevent ventricular stretching during the expansion phase of the intraventricular chamber (IVC) and ventricular stretching is allowed only during the diastolic refilling phase, the prevention of wall stretching is implemented by the same algorithm that regulates IVC expansion (FIG. 5).

Figure 7:
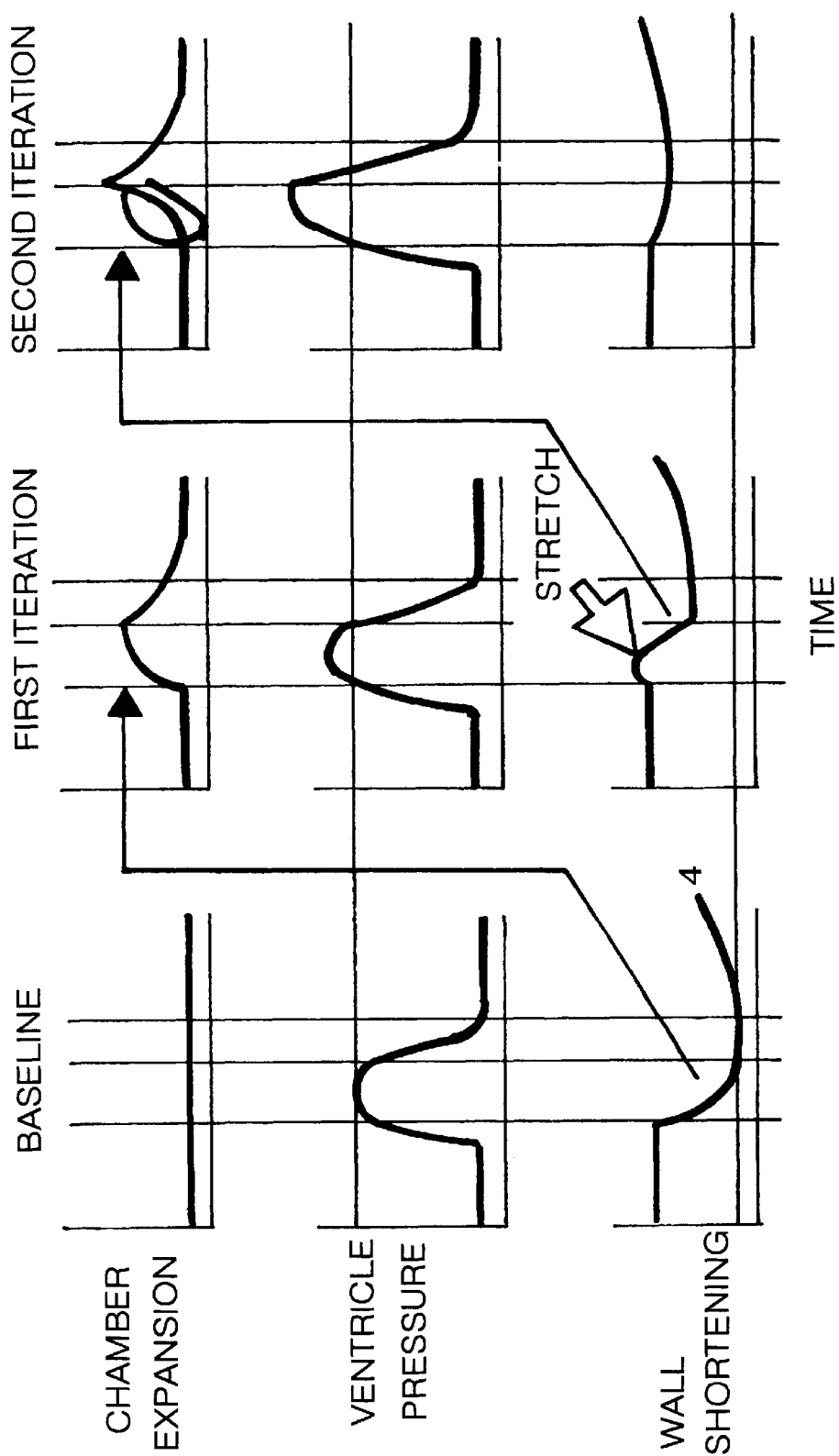
FIG. 7 is a diagram explaining the operation of the invention.

As soon as wall stretching is detected, the inverted function is added to the last function of the IVC expansion and is eliminated in successive beats. (see also FIGS. 5 and 7). The device works far from maximal power and thus far from the limits of ventricle wall motion where wall stretching may appear, so that some wall shortening will always remain. This ensures the safety and a reduced probability of causing damage to the ventricle wall.

In the algorithm of FIG. 6, an operator can determine the exact function of the expansion of the IVC. That function may be the exponential function or a ramp function or constant velocity or any other expansion function including polynomial functions. The operator, therefore, determines the profile but the magnitude is determined based upon beat-to-beat analysis of the ventricle wall shortening. If the IVC expansion does not cause ventricle wall stretching and there is still detectable ventricle wall shortening, then the amplification factor is greatly increased (on a beat-to-beat basis). The iteration is repeated until the desired cardiac output is reached or ventricle wall shortening diminishes to a point that a further increase in the size of the IVC might cause ventricle wall stretching.

Ventricle wall lengthening can trigger an alarm and the amplification factor ($A_F$) at the next beat is reduced to a provisional used value or by a certain percentage whereupon operation can continue without danger. The end of IVC expansion in this embodiment is determined by the earlier of a time set by the operator and closing of the ventricle outlet valve.

According to the invention the contracting phase of the IVC is controlled so that ventricle wall shortening is at a maximum while pressure is generated by the ventricle wall. Rapid wall shortening during pressure generation leads to rapid deactivation of the cardiac muscle and increased ventricle compliance. The IVC contraction expedites opening of the ventricle inlet valve, faster ventricle refilling and faster decompression of intramiocardial pressure (IMP) which improves coronary flow.

The parameters of the IVC contraction are: onset time of contraction, rate of contraction and total volume. The time onset of IVC contraction is triggered by the detection of the ventricle outlet valve closure, which reflects the end of ejection. Earlier contraction diminishes the cardiac output while contractions that occur later in the relaxation phase have less effect on the rate of wall relaxation (increase in ventricle compliance). This is done in real time based on the measurements previously described.

There are upper and lower limiting rates of the IVC contraction. The practical rate of contraction should be near the upper limiting rate so that the rate of IVC contraction should be effective in causing cardiac muscle deactivation.

The maximal rate of deactivation is achieved when the ventricle wall shortening is close to the maximal rate of cardiac muscle shortening. (The maximal rate of cardiac shortening is around 6 muscle-lengths per second, and is limited by the inherent properties of the cardiac motor units—the crossbridges). The maximal velocity of muscle shortening is reached when the muscle is unloaded (shortening against zero load).

A faster rate of shortening causes only muscle buckling. Hence, the simplest way to produce the rapid contraction is to expose the IVC to the near zero intra-thoracic pressure. The high ventricle cavity pressure (above 60 mm Hg) will compress the IVC without the need of additional external power supply (passive contraction). Active contraction is required only when there is significant resistance to flow of fluid (gas) from the intraventricle chamber to the extraventricular chamber due to a narrow connecting tubing system.

The lower rate of IVC contraction is limited by the duration of the diastolic period. The contraction should be terminated before the next cardiac beat. The lower rate is determined by the heart rate.

The total volume of contraction is controlled to be equal to the volume of expansion, so that the IVC works in a repeatable cyclic mode.

Note that no tight control of the profile of contraction is required, since there is no evidence that rapid shortening can damage the ventricle wall integrity.

Consequently, the profile of contraction can be as simple as possible, as a sigmoid function of time (acceleration, constant velocity of contraction, deceleration).

The detection of the time onset of expansion and contraction is done in real time (time response of 1 millisecond) by utilizing at least one of the following data acquisitions of cardiac mechanics, that allows determination of whether the ventricle outlet valve is open or closed via an apparatus as shown in FIG. 2:

a. The intraventricular pressure and the aortic pressure, or the gradient between the two.

b. The ventricle outlet flow, that can be measured by a flowmeter (as an ultrasonic or electromagnetic flowmeter) or by utilizing the Doppler effect.

c. The intraventricular volume—by ultrasound or electrical impedance measurements (impedance catheter).

d. The ventricle diameters, as for example by ultrasonic sonocrystals.

e. Ventricle wall shortening—as by strain gages.

f. Heart valve sounds—that reflects the opening and closure of the outlet valve. Note that the electrical activity of the myocardium (ECG) may also be used. However, it is not considered as a precise means for determining the precise time course of cardiac mechanics.

The detection of the time onset of expansion can precede the opening of the ventricle outlet valve when there is cardiac wall inhomogeneity (as in case of cardiac aneurysm—a scar tissue that may bulge out during the systole). In that case, the IVC function can be optimized based on the mechanical function of the preserved functional ventricle wall (myocardium). Consequently, the timing and the profile of contraction are determined also based on regional mechanical parameters, as the ventricle diameters or distances between anatomical points (markers) on the ventricle wall, for example the distances between ultrasonic sonocrystals, or local measurements of ventricle wall shortening—as by strain gages.

The IVC may be filled by fluid ro gas, but it is recommended to use a physiological solution. It is possible to use physiological solutions since the amount of fluid is small (less than 100 ml in both intraventricular and extraventricular chambers) and the kinetic energy spent for the fluid flow is relatively small. The device is implanted near the heart, so that the intra and extra-ventricle chambers are in close proximity (several cm), unlike the pneumatic systems (intra-aortic balloon, pneumatic assist devices). The mechanical time delays are in the order of milliseconds. An advantage of using physiological solutions is safety: leakage of physiological solution from the IVC causes no harm to the patient (in contrasts to leakage of gas into the blood in the other pneumatic devices (aortic balloon, pneumatic VAD). Another advantage lies in smoothing the balloon expansion and contraction profiles. The mass and the viscosity of the fluid (unlike gas) damps the high velocity oscillations of the system. Motion oscillations are very dangerous since volume oscillation (vibration) deteriorates ventricle wall capability to generate pressure.

The computer-controlled pump connected to the intraventricular chamber can be a simple syringe type used, where the position of the piston of the syringe is computer-controlled or by a computer-controlled bellows (pneumatic or hydraulic) or a flexible diaphragm.

The drive motor for the pump motor may be of various types, but should be able to allow high speed of operation (in the order of linear motion of 400 mm/sec), and should have low energy consumption and high efficiency, to reduce the heat dissipation and to allow implantation. The motor can be any electrical motor, e.g. a direct-current linear motor or voice coil. The motor can also be a transplanted heart, from human or animal source (pig). The advantage of this mode of heart transplantation, where the implanted heart is used as the motor that assists the natural failing heart, and does not replace it, are that the motor is very efficient and economical and there is no need for power supply (except for the control and excitation units), the natural heart is not taken out, and will always remain in place, eliminating the problem of rejection of the implanted heart, the operation procedure is simpler compared to regular heart translantation).

The extra-ventricular chamber is inserted into the implanted heart through the inlet or outlet valve orifices of the implanted heart. The coronary circulation of the implanted heart is connoted to one of the patient's arteries and the right auricle (to which the myocardial veins are drained) is connected to one of the patient's veins. The system can be repeated in case of need (rejection), compared to the regular heart transplantation.

The actuator can also be a patient's own skeletal muscle that is wrapped around the extraventricular chamber.

The intraventricular chamber may be of various types and shapes. It may be an elastic balloon that expands and stretches upon inflation or a compressive balloon that collapses upon deflation while the surface of the balloon is constant during expansion and contraction (similar to the intra-aortic balloon). It may contain one element or several elements in order to resemble the shape of the ventricle cavity and not to interfere with the tissue structures inside the ventricle cavity (trabeculae-muscle fibers or chordee tendinee that connect the valve leaflets to the papillary muscle). Note however, that the issue of the shape of the IVC is of minor importance, since the volume of the failing heart is in the order of 200–300 ml and even greater, while the maximal practical volume of the balloon is about 30 ml, so that there is enough space for the IVC to float inside the ventricle cavity.

Major Advantages of the Invention:

1. It is based on the physiological intracellular control of contraction, and allows optimization of the physiological heart function. The residual mechanical activity of the heart is utilized, so that the required additional external work is minimed (i.e. smaller device, smaller energy consumption).

2. It generates smaller forces (about tenths of needed forces in analogue devices as direct mechanical ventricular actuation) due to the smaller surface of the intraventricular chamber (i.e. smaller device, smaller energy consumption).

3. It improves both the systolic and diastolic function of the failing heart.

4. No need for artifical valves since it utilizes the biological valves (less thromboembolic complications).

5. It has a small surface area in contact with blood, and the blood is not propelled through a pump (less thromboembolic complications).

The results of the method of the invention are:

1. Increase in the cardiac output—due to the combined effect of IVC expansion and cardiac wall shortening.

2. Increase in the aortic pressure—mainly since the device reduces cardiac shortening and the accompanied decreases in the ability of the physiological heart to generate pressure.

3. Decrease in the end-diastolic volume—due to the improved cardiac output and decreasing the preload.

4. Decrease in the energy consumption of the heart and increase in cardiac efficiency, due to the decrease in the end-diastolic volume and the increase in the generated external work (including the shortening during the diastole), shown in FIG. 4.

5. Slow remodeling of the ventricle geometry and gradual decrease in the ventricle size due to the decrease in the end-diastolic volume and the decrease in energy consumption. This may provide the basis for using the device as a bridge to recovery and not only as a bridge to transplantation. However, this can be only verified clinically.

The IVC is implanted into the ventricle cavity through the ventricle wall, after exposing the ventricle by left thoracotomy. The device is introduced through the ventricle apex, when the heart failure is due to dilate cardiomyopathy or other diseases that cause homogeneous decrease in the left ventricle shortening. If there is segmented inhomogeneity, other locations may be considered, also in combination with aneurismectomy or partial ventriculectomy of the malfunctioning segment. In general, the IVC can be implanted into the left ventricle at any site of the wall that allows easy access and no interference with papillary muscle or ventricle valve apparatus or the cardiac circulatory or conductive systems. Hence, the surgery procedure is almost minimally invasive,and is widely used at the clinics. Also, the implantation of the device through the apex is not unacceptable. Most of the cannulas that are used for draining the ventricle are introduced through the apex.

A typical validation setup is shown in FIG. 2. An example of application of the invention to a pig model is given below.

The anesthesia of the pigs is maintained by Fentanyl (Beatryl) (10 mgr/kg/hour) with Pancuronioum (0.2 mg/Kg/hour). Two millars transducers (pressure transducers) are used, one is inserted into the LV cvity and the second is placed in the aortic arch. For feasibility studies, the transducers are inserted percutaneously through major arteries. However, the final device will include an attached pressure gauge on the IVC.

During the studies the heart was exposed by mid-line sternotomy and pericardiotomy. However, the final device will be implanted by left thoracotomy that will only expose the ventricle apex, and will be introduced into the ventricle cavity by minimal invasive procedure.

The intraventricular chamber (IVC) is implanted into the left ventricle cavity via the apex, and is connected via an 8 nm tube (in diameter) to the extra ventricular chamber or to the syringe (FIG. 2) during the feasibility study. The intraventricular chamber (IVC) is made of silicon during the animal experiment studies, but is made of blood biocompatible materials (as polyurethane in the intra-aortic balloon) in the device for human application.

Figure 8:
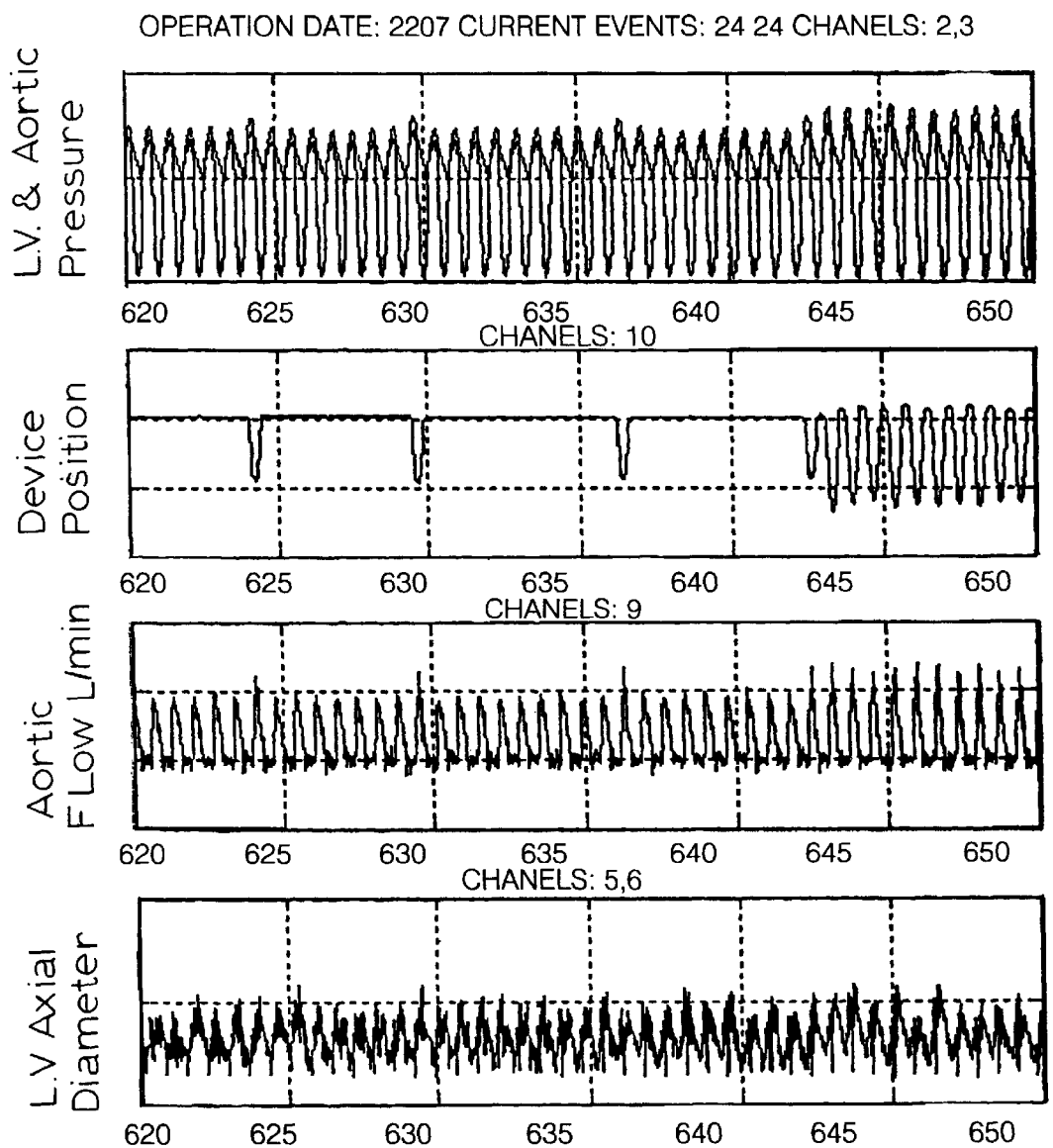
FIG. 8 represents results from imposed volume changes of the intraventricular device.

The piston of the syringe is held by an external motor. The motor (for the feasibility study, a Pacific scientific stepmotor and controller are used) allows imposition of volume changes in the intraventricular chamber (IVC). The profile of the IVC volume changes, i.e. the piston displacement (rate of inflation and deflation, duration, maximal volume) are determined by the programmable motor. These parameters are entered to the motor controller between consecutive beats. Hence the computer-controlled system allows imposition of different volume changes and various profiles of volume changes. In contrast, the onset time of inflation and deflation are determined in real time, by a real time program (LabView is currently used during the 10o feasibility study). The timing of the imposed volume changes is synchronized with the ejection phase of contraction (as shown in FIG. 4). FIG. 8 presents the effect of the controlled IVC volume changes (second row) on the cardiac outflow, i.e. the rate of blood ejection into the aorta (aortic flow) and the generate pressure (top row). The effect of the device is shown both for single beat intervention, where the IVC was activated only during one cycle to test whether it disturbs the normal ventricle function, and for prolonged and continuous operation. No real time feedback loops are used in order to avoid vibration. However, the profile of the volume changes is continuously evaluated based on the obtained pressure, flow and left ventricle diameter changes. The parameters of the volume changes (velocity, acceleration) are under continuous adaptive control.

An occluder 32 (FIG. 2) is placed around the ascending aorta only during the feasibility study. This will allow evaluation of cardiac performance, the maximal pressure that can be generated by the heart.

The LV diameters are measured by sonomicrometers 28 (FIG. 2) (Triton Tech. Inc. model 200–1000), implanted into the LV wall. The sonomicrometer is used to measure precisely the ventricle diameter during the feasibility study. The sonomicrometers create an orthogonal three-dimensional grid (anterior-posterior, septum-lateral and apex base) that will be used for the evaluation of the LV volume. The final device will include conductance electrodes on the IVC, which will allow the measurement of the ventricle volume. This parameter provides additional important information that allows verification that no stretch is imposed on the ventricle wall ("eccentric work").

A flowmeter 31 (FIG. 2) is placed around the aortic arch to record the aortic flow in order to quantify the effect of the device on the cardiac output and for monitoring the onset and offset time of ejection.

The onset of the ejection phase and the closure of the aortic valve were detected during feasibility studies:

1. From the analysis of the relationship between the intraventricular pressure and the aortic pressure.
2. From the left ventricle diameter changes, measured by the sonocrystals or the conductance catheter.
3. From aortic flow and from monitoring the heart sound (less likely).

All of these measurements add further information for the precise determination of the trigger timing, during the feasibility study. However, only one of these methods is sufficient for the final device. The results presented here (FIGS. 8–10) are based on a trigger signal, which is derived from a simple subtraction of the ventricle pressure from the aortic pressure. In the final device these sensors; pressure transducer, sonomicrometer (distance), Doppler measurement (flow) and conductance (volume) will be attached to the IVC.

Six experimental studies have been performed using 3-months old pigs (body weight of about 32 Kg) to validate the suggested method and the results are satisfactory. Note the marked increase in the peak aortic flow and the ventricle and aortic pressure (FIG. 8), both for a single beat mode of operation and during continuous mode of operation. Although we have used only small volume changes, of 8 ml, a significant increase in the cardiac output is observed. The peak aortic flow increases by approximately 30 percent and the stroke volume increased by 6 ml per beat, i.e. by more than half a liter per minute for a pig with cardiac output of 2.5 1/min.

Moreover, our recent study with failing pig heart has demonstrated an even stronger effect and an increase in the cardiac output of the failing heart from 1.5 to 2.3 1/min (about 50%) and almost to the normal cardiac output ranges.

Figure 9:
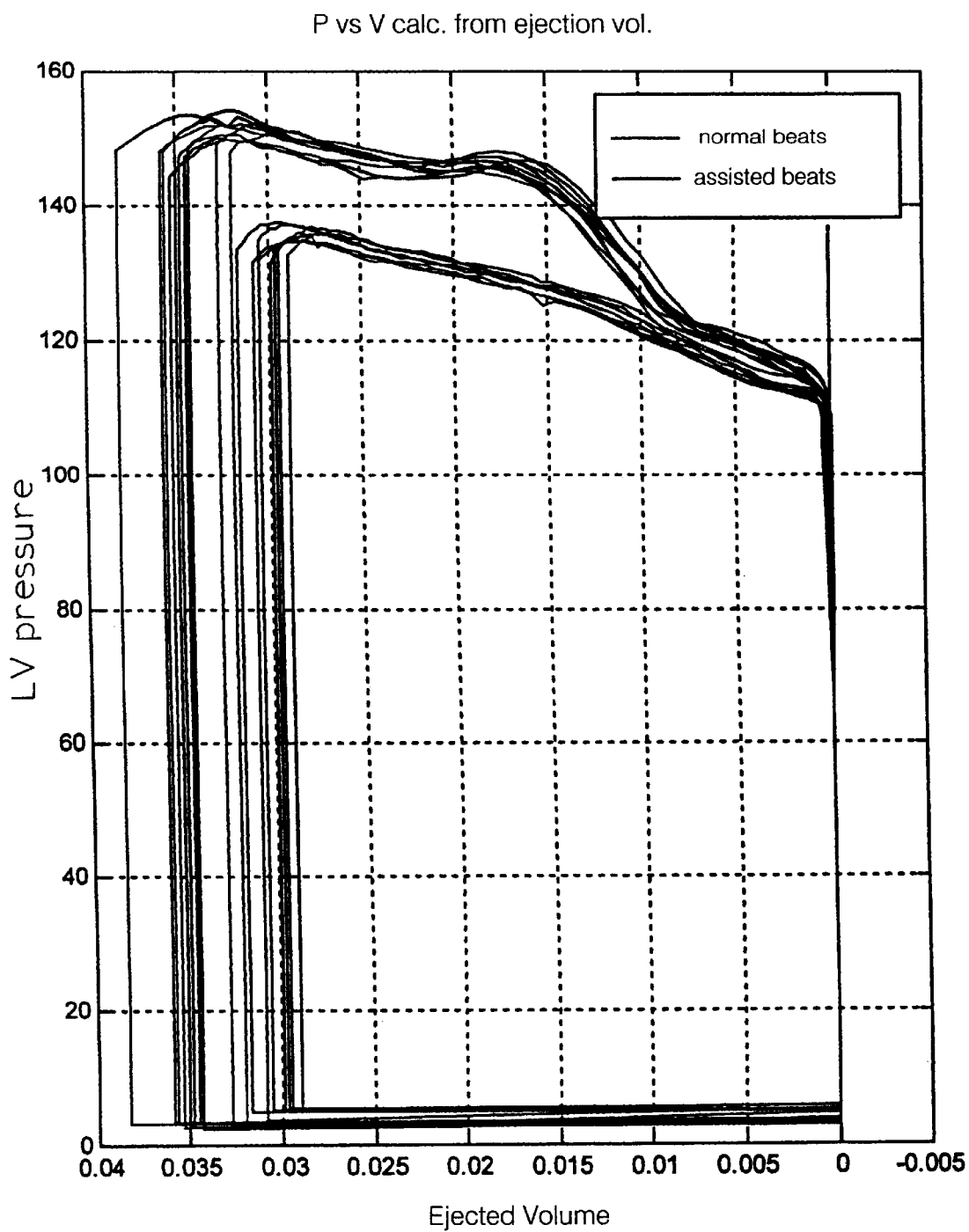
FIG. 9 is a diagram illustrating the external work during normal and assisted beats.

FIG. 9 represents the work done by the heart during normal (blue) and assisted (red) beats. The area inside the pressure-volume loops present the generated external work. Note the increase in the peak systole pressure during the assisted beat (154 vs. 137 mm Hg), and the increase in the ejected volume (35 ml vs 30). This increase in the external work is due to the added work done by the assist device (items 3 Section 3.3).

Figure 10:
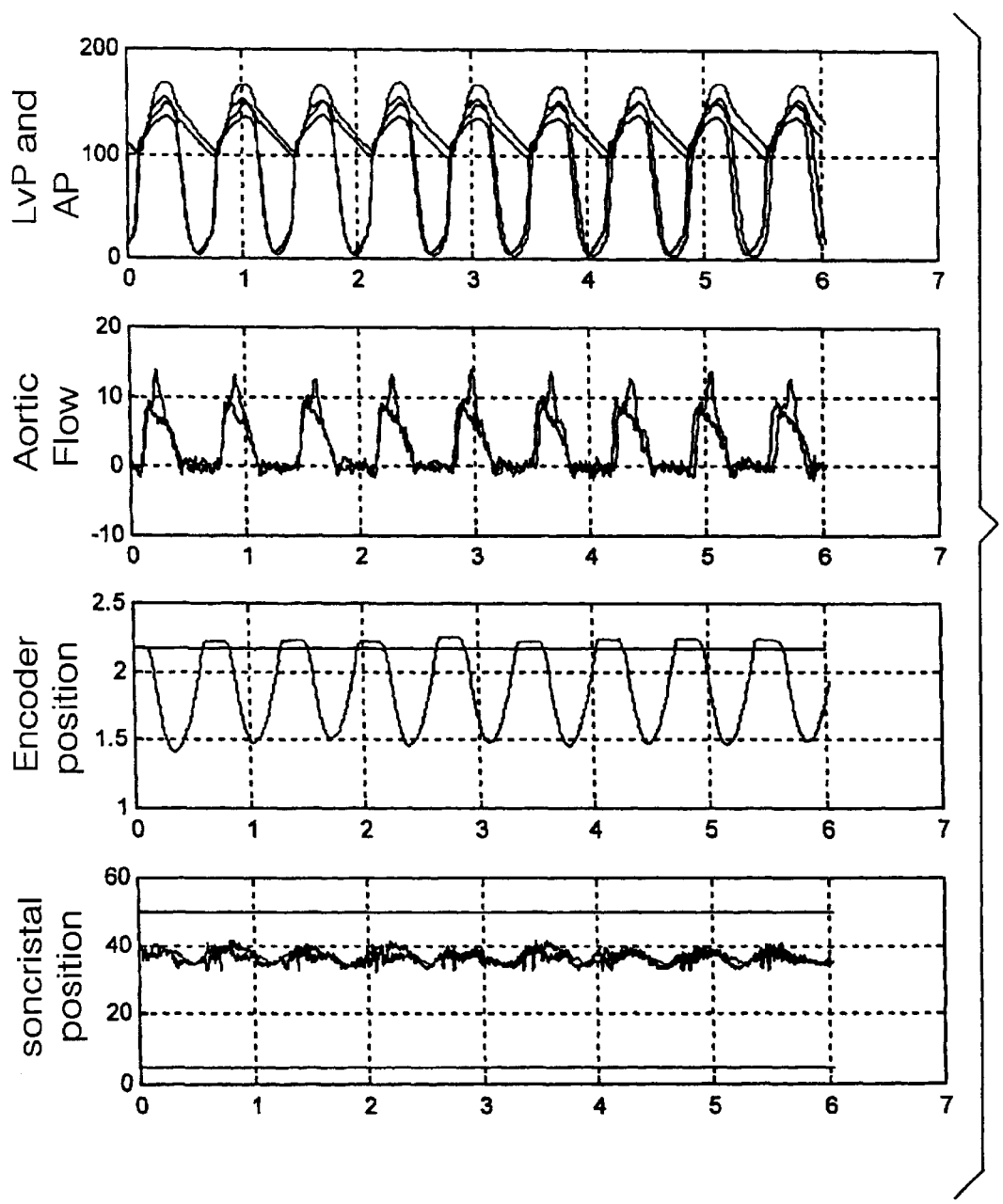
FIG. 10 is a set of diagrams illustrating ventricle pressure, aortic pressure, aortic flow and ventricle diameter during natural and assisted beats.

The effect of the suggested device on cardiac hemodynamic is presented also in FIG. 10 where the measurement during assisted circulation was overlaid on the measurements during the normal contractions. Note the significant increase in the aortic flow (second trace) and the increase in the aortic pressure.

I claim:

1. A ventricular assist method which comprises the steps of:
    (a) inserting into at least one failing ventricular cavity of a failing heart through a wall thereof a respective expandable intraventricular chamber;
    (b) in cadence with normal functioning of said failing heart, effecting expansion of said intraventricular chamber with each heart beat and commencing only after opening of an outlet valve of the respective ventricular cavity of the failing heart or only after a detected shortening of a monitored region of a wall of the respective ventricular cavity of the failing heart and continuing during an ejection phase of the respective ventricular cavity, thereby augmenting ejection volume from the respective ventricular cavity by up a maximum volume of the intraventricular chamber per systolic phase;
    (c) monitoring ventricular ejection or a ventricular wall region for shortening and controlling a course of expansion of each said intraventricular chamber in step (b) to reduce a shortening and at the same time to prevent stretching of a respective monitored ventricular wall region of the failing heart by comparison with ventricular wall shortening prior to insertion of the respective intraventricular chamber; and
    (d) depressurizing and contracting each said intraventricular chamber immediately upon closing of a respective said outlet valve of the failing heart.

2. The method defined in claim 1, further comprising the steps of:
    measuring parameters of ventricular wall motion during systole and the expansion of a respective intraventricular chamber in step (b) and parameters of global cardiac function; and
    applying and controlling a profile of the expanding intraventricular chamber in a course of expansion thereof to decrease the measured ventricular wall motion thereby obtaining an increase in pressure within the respective ventricular cavity and an increase in the cardiac output.

3. The method defined in claim 1, further comprising the steps of:

monitoring at least one parameter of ventricular wall shortening and at least one parameter of ventricular output during systole; and in response to measurement of said parameters of ventricle wall shortening and ventricular output and selectively either in real time or by beat-by-beat computation, determining a desired shape of each said intraventricular chamber during expansion thereof; and controlling the shape and a rate of expansion and a rate of contraction of the respective intraventricular chamber during step (b) to correspond to said desired shape.

4. The method defined in claim 3 wherein said ventricular diameter is measured as a measurement of ventricle wall shortening or as a measurement of ventricular volume change.

5. The method defined in claim 3 wherein ventricular volume is measured as a measurement of ventricle wall shortening or as a measurement of ventricular output.

6. The method defined in claim 3 wherein said parameter is ventricular wall strain and is measured as a measurement of ventricle wall shortening.

7. The method defined in claim 3 wherein said parameter is ventricular flow and is measured as a measurement of ventricle wall shortening.

8. The method defined in claim 3 wherein each said intraventricular chamber is a balloon and the expansion of each said intraventricular chamber is effected by fluid expansion of the respective balloon with a physiological solution.

9. The method defined in claim 8 wherein a said balloon is implanted into the failing ventricle cavity at the apex thereof or at another site of a respective wall affording access without interference with papillary muscle and ventricle valve apparatus or cardiac circulatory or conductive systems.

10. A ventricular assist apparatus comprising:

an expandable intraventricular chamber insertable into a ventricular cavity of a failing heart through a wall thereof;

means including a computer-controlled actuator connected to said intraventricular chamber for effecting expansion and contraction of said intraventricular chamber in cadence with normal functioning of said failing heart and commencing only after opening of an outlet valve of the respective ventricular cavity of the failing heart or only after a detected shortening of a monitored region of a wall of the respective ventricular cavity of the failing heart and continuing during an ejection phase of the respective ventricular cavity, thereby augmenting ejection volume from the respective ventricular cavity by up to a maximum volume of the intraventricular chamber per systolic phase; and at least one sensor for monitoring wall shortening of said failing ventricle, said sensor being connected to said computer-controlled actuator and controlling a course of expansion of said intraventricular chamber.

11. The apparatus defined in claim 10 wherein said means including said computer-controlled actuator includes means for monitoring parameters of ventricle wall shortening and cardiac output, and means for correcting an expansion function of said intraventricular chamber based upon a difference between desired and monitored cardiac output using a predetermined feedback amplification factor.

12. The apparatus defined in claim 10, further comprising a computer receiving input from said sensor and connected to said actuator, said computer controlling said actuator with an output, said computer being programmed for each heartbeat (n) to:

(a) evaluate cardiac output and work at the n beat;

(b) compare the evaluated cardiac output and work at the n beat with a desired cardiac output to determine an amplification factor ($A_F$) constituting a gain of a feedback loop which determines a rate at which a function of intraventricular chamber expansion will be corrected to achieve a desired cardiac output;

(c) multiply the amplification factor ($A_F$) by a predetermined weighting function (W(t)) to enable an operator to determine a magnitude of feedback;

(d) evaluate ventricle wall shortening ($S_n(t)$) and compare the evaluated wall shortening with a desired wall shortening (Des(t)) to obtain an incremental correction profile $Err_n(t)=Des(t)-S_n(t)$;

(d) generate an expansion function $EXP_{n+1}(t)=EXP_n(t)+A_F*W(t)*Err_n(t)$; and (e) control expansion of the intraventricular chamber at a next beat (n+1) with said expansion function $EXP_{n+1}(t)=EXP_n(t)+A_F*W(t)*Err_n(t)$.

13. The apparatus defined in claim 12 wherein said computer is an implantable computer which controls the intraventricular chamber at the next beat (n+1) with a predetermined expansion/contraction function by regulating onset time of expansion/contraction and a function of expansion, the expansion/contraction function being calculated between heartbeats before an onset of a next beat, the apparatus including means for detecting the onset time in real time.

14. The apparatus defined in claim 12 wherein said weighting factor (W(t)) is a function of time determined by said operator where $0 \leq W(t) \leq 1$ when $0 \leq t \leq T$, and t=0 is the onset of expansion and t=T is the end of expansion.

15. The apparatus defined in claim 10, further comprising a computer receiving input from said sensor and connected to said actuator, said computer controlling said actuator with an output, said computer being programmed for each heartbeat (n) to:

(a) evaluate cardiac output and work at the n beat;

(b) compare the evaluated cardiac output and work at the n beat with a desired cardiac output and determine an amplification factor that will not cause wall stretch in part based upon additional inputs;

(c) evaluate ventricle wall shortening ($S_n(t)$) at said n beat and providing the ventricle wall shortening as one of said additional inputs;

(d) detect possible ventricle wall lengthening from the evaluation of the wall shortening in step (c) and providing therewith another of said additional inputs, and triggering an alarm upon ventricular wall lengthening (f) from the amplification factor and a desired profile of expansion, determine a time course of expansion of the intraventricular chamber; and (g) generate an expansion function representing the time course of expansion control expansion of the intraventricular chamber at a next beat (n+1) with said expansion function.

16. The apparatus defined in claim 10, further comprising a computer connected to said actuator and wherein said computer actuator is programmed to initiate expansion of said intraventricular chamber upon detection of an outlet valve opening or significant shortening of the monitored ventricle wall in real time.

17. The apparatus defined in claim 10 wherein said computer-controlled actuator is programmed to initiate contraction of said intraventricular chamber upon detection of an outlet valve closure in real time.

18. The apparatus defined in claim 17 wherein said computer-controlled actuator is programmed to connect said intraventricular chamber to intrathoracic pressure and said computer-controlled actuator includes a compressible extraventicular chamber and connection tubing between said extraventricular chamber and said intraventricular chamber.

19. The apparatus defined in claim 10, further comprising means for detecting opening and closure of said outlet valve and including at least one of the following:

means for measuring intraventricular and aortic pressure or a gradient between intraventricular and aortic pressure;

a Doppler or an ultrasonic or electromagnetic flowmeter measuring ventricle outlet flow;

ultrasound or electrical impedance means for measuring intraventricular volume;

strain gauge means for measuring ventricle wall shortening; and means for detecting heart sounds.

20. The apparatus defined in claim 10, further comprising means for monitoring timing and profile of intraventricular chamber expansion based on a detection of regional ventricle wall motion, to optimize the apparatus based on a preserved measured functional region of the ventricle wall, said means for monitoring including at least one of the following:

means for measuring ventricle diameters or distances between anatomical points on the ventricle wall; and means for measuring local changes in strain in the ventricle wall.

21. The apparatus defined in claim 10 wherein said actuator is selected from the group which consists of a syringe pump, a bellows or a flexible membrane, and an actuator motor operating said actuator.

22. The apparatus defined in claim 21 wherein said actuator motor is selected from the group which consists of an electric motor and a contractile motor.

23. The apparatus defined in claim 22, further comprising a computer connected to said actuator and said at least one sensor on said intraventricular chamber for measuring a volume thereof and an additional sensor on said intraventricular chamber for measuring ventricle pressure, said sensors being connected to said computer.

24. The apparatus defined in claim 10, wherein said sensor includes at least one sonomicrometer adopted to be attached to or implanted in said ventricle wall.

* * * * *